United States Patent [19]

Peetermans

[11] 3,953,592

[45] Apr. 27, 1976

[54] LIVE INFLUENZA VIRUS VACCINES AND PREPARATION THEREOF

[75] Inventor: Julien Peetermans, Rixensart, Belgium

[73] Assignee: Recherche et Industrie Therapeutiques (R.I.T.), Belgium

[22] Filed: Sept. 27, 1973

[21] Appl. No.: 401,335

[52] U.S. Cl. .................................. 424/89; 195/1.5
[51] Int. Cl.[2] .................................. A61K 39/12
[58] Field of Search .................................. 424/89; 195/1.1–1.5

[56] References Cited

OTHER PUBLICATIONS

Krizanova et al., *Current Topics in Microbiology and Immunology*, Vol. 47, pp. 125–151, 1969.
Murphy et al., *The Journal of Infectious Diseases*, Vol. 126, pp. 170–178, Aug. 1972.

*Primary Examiner*—Richard L. Huff
*Attorney, Agent, or Firm*—Alan D. Lourie; William H. Edgerton

[57] ABSTRACT

Stable $H_3N_2$ influenza virus strains completely resistant to serum inhibitors are obtained by passaging at least one time in the allantoic cavity of embryonated eggs in the presence of serum a recombinant strain previously obtained from an $H_3N_2$ influenza strain and the $A/PR_8$ influenza virus strain and isolating the so-obtained serum inhibitors resistant strains. The obtained strains are useful for vaccine production.

8 Claims, No Drawings

LIVE INFLUENZA VIRUS VACCINES AND PREPARATION THEREOF

This invention relates to a process of preparing stable $H_3N_2$ influenza virus strains completely resistant to serum inhibitors and to live influenza virus vaccines containing them.

Protection against viral respiratory infections has been shown to be related to the presence of a local immunity in the respiratory mucosa. This aspect has been reviewed recently by Rossen et al. (Progr. Med. Virol. 1971, 13, 194).

Several attempts were made in recent years to induce immunity against influenza by the intranasal application of inactivated vaccines (see e.g.: Waldman et al. Nature, 1968, 218, 594: J. Immunol. 1969, 207, 520: WHO Bull. 1969, 41, 543). The results were inconsistent, however, and this was probably due to the insufficient stimulation of the immunity system by the inactivated antigen (Tyrrell et al. J. Hyg. 1970, 68, 359).

Live influenza vaccines are also known but presenting different protection rates and numerous efforts have been made —e.g. by serial passages on eggs— to reduce pathogenicity of the virus.

Such influenza vaccines have been used in the Soviet Union for several years and, according to Smorodintsev et al. (Bull. WHO, 1969, 41, 585) good protection was conferred in the face of influenza epidemics.

From clinical trials conducted with viruses isolated from patients in the hope that some of these viruses would prove non-pathogenic (A. A. Smorodintsev, G. A. Alexandrova, O. M. Chalkina and A. A. Selivanov, Applied Virology (1965): 1st Annual Symposium, Boca Raton, Florida, 1964, edited by M. Saunders and E. H. Lennette, p. 142 Sheboygan, Wisconsin, Ellis), it has been concluded that the viruses resistant to horse serum inhibitors cause fewer reactions than those which are sensitive to horse serum inhibitors.

It is however admitted that, in order to eliminate the side reactions upon administration of an influenza live virus vaccine, the conversion to inhibitor resistance must be complete as the persistence of even a small percentage of inhibitor — sensitive particles may render a virus too pathogenic for human use. Different attempts have been made to isolate influenza virus strains completely resistant to horse serum inhibitors and techniques have been described for improving the inhibitor resistance of influenza viruses, said techniques consisting essentially in passaging serially influenza virus strains in eggs in the presence of serum.

Allantoic passages of mixtures of a given dose of influenza viruses and horse serum have been proven to result in complete horse serum resistance of $A_2$/England/501/68 ($H_2N_2$) influenza virus strain while the results were non conclusive for $A_2$ Hong-Kong ($H_3N_2$)/1/68 virus strain (A. S. Beare, and M. L. Bynoe, British Medical Journal 4, 198–201, 1969).

It is also known that allantoic passages of mixture of a given dose of influenza virus $A_2$ Hong-Kong ($H_3N_2$)/1/68 and guinea pig serum gives no positive results before the 17th passage (D. Ikic, N. Pasini, N. Rajner, B. Jancikic, M. Juzbasic and M. Hecimovic, Proc. Symposium on Acute Respiratory Diseases, 1969, Yugoslav Academy of Sciences and Arts, Zagreb).

It has also been demonstrated that it is possible to complete the inhibitor resistance within a limited number of passages when using successively horse serum and guinea pig serum in the passages, i.e. that it is possible to obtain a stable and immunogenic $A_2$ Hong-Kong ($H_3N_2$) influenza virus strain completely resistant to serum inhibitors when subjecting to serial passages in the allantoic cavity of eggs in the presence of increasing concentrations of guinea pig serum an $A_2$ Hong-Kong ($H_3N_2$) influenza virus strain which has previsouly been serially passed in the allantoic cavity of eggs in the presence of increasing concentrations of horse serum.

We have now found that stable $H_3N_2$ influenza virus strains completely resistant to serum inhibitors and valuable for vaccine use by intranasal administration are obtained when a recombinant $H_3N_2$ influenza virus strain obtained by recombination from a $H_3N_2$ influenza virus and an A/$PR_8$ influenza virus is passaged in the allantoic cavity of embryonated eggs in the presence of serum, the eggs being preferably chicken eggs and the serum being preferably guinea pig serum.

Recombinant $H_3N_2$ influenza virus strains obtained by recombination from $H_3N_2$ influenza viruses and the A/$PR_8$ influenza virus strain are known.

It then becomes possible to select from those recombinants virus clones having high growth capacity (E. D. Kilbourne, Bull. Wld. Hlth. Org. 41, 643–645, 1969). Some virus clones isolated from such recombinations have been shown to be attenuated for man; nevertheless neither in vitro nor in vivo markers correspond with attenuation, and the attenuated properties of the different virus clones have to be tested by the infection of humans (A. S. Beare and T. S. Hall, Lancet 1971 II, 1271–1273). In the process of our invention, a recombinant $H_3N_2$ influenza virus strain, selected for having high growth properties, is made resistant to serum inhibitors. The so-obtained modified influenza virus, having the $H_3N_2$ antigenic composition, has maintained its high growth capacity. Thus, we have developed a candidate live influenza vaccine for which no screening in humans is necessary to select the virus clones having an acceptable degree of attenuation and which possesses a stable in vitro marker. This candidate is obtained after only one or two passages of the selected recombinant, $H_3N_2$ influenza virus, in the allantoic cavity of embryonated eggs in the presence of serum inhibitors as indicated above.

An $H_3N_2$ influenza virus strain completely resistant to serum inhibitors obtained according to the process of this invention has been assigned the "Alice strain" designation in the applicant's collection and samples can be obtained upon written request to applicant's address.

Thus, the present invention relates to a process of preparing stable $H_3N_2$ influenza virus strains completely resistant to serum inhibitors —more particularly the Alice strain— which comprises passaging at least one time in the allantoic cavity of embryonated eggs —more particularly chicken eggs— in the presence of serum —more particularly guinea pig serum— a recombinant strain previously obtained from an $H_3N_2$ influenza virus strain —more particularly A/England/42/72 strain— and the A/$PR_8$ influenza virus strain —more particularly the Mount Sinai A/$PR_8$/34 strain — the cultures being carried out using different virus dilutions varying from $10^{-1}$ to $10^{-7}$ in normal saline in the presence of different serum dilutions varying from ¼ to 1/1000 in normal saline and isolating the so-obtained serum inhibitors resistant strains, preferably those obtained in the presence of the highest serum concentration and the lowest virus concentration.

Obviously, either the recombinant strain or the isolated resistant strain or both may be cloned or submitted to several dilution passages without modifying the essence of the invention.

So, the Alice virus strain is the one obtained from the MRC-2 clone previously submitted to 5 terminal dilution passages before being passaged once at a $10^{-3}$ concentration in the presence of a 1/16 dilution of guinea pig serum in normal saline and once at the $10^{-7}$ concentration in the presence of a ¼ dilution of guinea pig serum in normal saline and further submitted to 3 terminal dilution passages in the absence of serum plus one further passage in the absence of serum for seed lot production. This lot corresponds to the 12th passage of the MRC-2 clone, the strain used from the 7th passage onwards being resistant to serum inhibitors.

The so-obtained virus strains completely serum inhibitors resistant are non-pathogenic, immunogenic and valuable for influenza live virus vaccine production, using therefor any technique known to the art for live influenza production and/or stabilization. Consequently, the present invention also relates to attenuated influenza virus vaccines containing at least one said serum inhibitors resistant virus strain and to the process of preparing said vaccines therefrom.

According to this embodiment, the invention relates to a method of preparing an attenuated influenza virus vaccine comprising incubating in the allantoic cavity of embryonated chicken eggs a serum inhibitors resistant $H_3N_2$ influenza virus strain as obtained by the herein above described process, said incubation being for a period of time sufficient to permit growth of a large amount of said virus, and harvesting the resulting virus material.

The so-obtained attenuated influenza virus vaccines are administered topically in the nasopharynx.

For vaccinal use, the virus is preferably kept in freeze-dried form and the vaccine is extemporaneously reconstituted by addition of either water of any other pharmaceutical diluent or composition known to the art for the preparation of nasal preparations such as drops or spray.

The following examples illustrate the present invention; they should not be construed as limiting its scope.

EXAMPLE 1

Procedure

A sample of MRC-2 clone submitted to 5 terminal dilution passages and shown to be highly sensitive to normal serum inhibitors is used as starting viral material. Different dilutions (i.e. $10^{-1}$, $10^{-3}$, $10^{-5}$ and $10^{-7}$) of said starting viral material in normal saline are mixed with different dilutions (i.e. ¼, ⅛, 1/16, 1/40, 1/200 and 1/4000) of sterile normal guinea pig serum (in normal saline) previously adjusted at the ¼ dilution and then maintained for 15 minutes in a boiling water bath further diluted, homogenized and centrifuged at 2,000 rpm for 30 minutes. The supernatant is used for the further step which consists in incubating the virus/-serum mixtures at 37° C for 1 hour before inoculating 0.2 ml. aliquots of said mixture into the allantoic cavity of a series of embryonated chicken eggs previously incubated for 9 to 10 days at 37° C and candled (only the surviving eggs are inoculated).

The eggs are then further incubated for a period of time varying between 24 and 96 hours.

At the end of this incubation period, the eggs are candled and the surviving eggs are chilled at 4° C. The allantoic fluid of each series of surviving eggs is harvested separately and tested for the presence of influenza virus by the hemagglutination method. The harvested virus produced by the inoculum of the highest virus dilution in the presence of the highest serum concentration which shows hemagglutination activity (i.e. virus dilution $10^{-3}$ and serum dilution 1/16) is used for a second passage performed in the same operative conditions. The harvested virus produced by the inoculum of the highest virus dilution (i.e. $10^{-7}$) in the presence of the highest serum concentration (i.e. serum dilution ¼) shows hemagglutination activity and is completely resistant to normal serum inhibitors as indicated in the following Table I.

Three further passages at terminal dilutions are carried out in the absence of serum to clone the obtained resistant mutant and to check the stability of the resistant character. As indicated in the following Table I, the virus harvested at each passage is completely resistant against the inhibitors of normal serum. The virus at the last passage level is used as inoculum for the production of the seed lot of the Alice strain. Therefore, the harvested allantoic fluids are collected and pooled, sterility and safety tested, mixed with peptone to reach a final concentration of 5% of peptone. A volume of 0.5 ml. of the viral suspension is distributed into 3 ml. vials and freeze-dried.

In Vitro and in Vivo Characteristics of the Modified Virus

1. Inhibitor resistance

For testing the resistance against the inhibitors present in normal heated animal serum (horse, guinea pig and calf serums previously heated at 75° C for 1 hour), serial twofold dilutions of the heated serums were mixed with 4 hemagglutinating units of the parent strain and the modified virus. After incubation of 1 hour at room temperature, chicken red blood cells were added and the results recorded. These results are shown in the following Table I:

TABLE I

| Serum | Parent Strains: $A_2$/Eng/ 42/72 | Parent Strains: MRC-2 | Modified virus: After 1st passage in the presence of serum | Modified virus: After 2nd passage in the presence of serum | Modified virus: After the 3rd terminal dilution passages | Alice strain seed lot | Alice strain Lot A | Alice strain Lot B |
|---|---|---|---|---|---|---|---|---|
| Horse | >10,000 | >10,000 | <20 | <20 | <20 | <20 | <20 | <20 |
| Guinea pig | >10,000 | >10,000 | <20 | <20 | <20 | <20 | <20 | <20 |
| Calf | 1,000 | 1,000 | <20 | <20 | <20 | <20 | <20 | <20 |

The data show a complete resistance for the seed lot and two consecutive experimental lots produced from this seed lot.

2. Stability of the inhibitor-resistant character

The resistant character of the Alice strain was confirmed in eggs and in laboratory animals (ferrets).

— in eggs, the Alice strain was submitted to 5 further passages in embryonated chicken eggs without alteration of its resistant character — in ferrets, the virus isolated 3 days after intranasal inoculation ($10^7$ $EID_{50}$) was also found completely resistant to serum inhibitors.

3. Antigenicity and absence of side effects

A first group of 4 ferrets was inoculated intranasally with $10^7$ $EID_{50}$ of the Alice strain. The temperature of the animals was taken daily during 5 days p.i. No significant temperature rise was recorded (maximum temperature 39.8° C). A second group of 2 ferrets was inoculated intranasally with $10^7$ $EID_{50}$ of the $A_2$/Eng/4272 parent strain. Two days after the inoculation the 2 animals showed temperatures of 40.8° C and 41.2° C respectively. A third group of 2 ferrets was inoculated intranasally with $10^7$ $EID_{50}$ of a strain isolated in Australia in 1972 ($A_2$/Victoria/101/72). Both ferrets showed a positive response on the 2nd day after the inoculation (temperatures higher than 40.5° C). Hemagglutination-inhibition tests demonstrated that the inhibitor resistance does not alter the antigenicity of the virus in ferrets: 14 days after the intranasal inoculation, serum antibody titers were very high among the inoculated animals (titer 1/1024 ) opposed to the control group (titer $>1/8$).

EXAMPLE 2

Starting from the freeze-dried material obtained in Example 1 (i.e. the Alice strain) as seed lot for large scale vaccine production, a further passage is carried out in the allantoic fluid of another set of embryonated chicken eggs which are incubated at 36° C for 3 days.

The allantoic fluids are harvested, pooled, sterility and safety tested, mixed with peptone in order to reach a final concentration of 5% of peptone and distributed into 3 ml. glass vials in order to obtain a dosage unit (i.e. at least $10^7$ $EID_{50}$) of virus. The product is then freeze-dried and the vials sealed or tightly stoppered.

This passage level is used as vaccine batch. For vaccine administration, the contents of one vial is reconstituted by adding 0.5 ml. of water or saline or a 5% sucrose solution and administered as drops in the nostrils.

Alternatively, the allantoic fluids peptone preparation is distributed in larger glass vials in order to obtain integers of the dosage unit amount of virus to constitute corresponding multi-doses vaccine preparations.

EXAMPLE 3

Vaccination with the attenuated influenza vaccine, Alice strain.

Material and Method.

Ten subjects, aged between 18 and 44 (average age: 28 years) and having an H.I. antibody titer ≤ 32, were selected for the trial. These 10 subjects received, with a 14 day interval, two administrations of the extemporaneously reconstituted vaccine, Alice strain. For each administration, all subjects received the vaccine obtained in Example 2 (5 drops per nostril). Nasal washings and blood samples for antibody determination (A/England 42/72 strain) were taken on day 14 after the first administration (i.e. the day of the second inoculation) and 3 to 4 weeks after the second administration.

Results.

I. Clinical

Temperature was recorded for 5 days following each administration. As indicated in the following Table II, only one subject (No. 3) presented a slight elevation of temperature (37.2° C on day 1).

Seven subjects showed some mild clinical manifestations: six of them had a serous rhinitis or nasal congestion for one to two days and one subject complained of mild headaches with pharyngeal hypersecretion.

II. Virus isolation

Nasal and throat swabs were collected on day 2 in eight subjects (Nos. 3, 5, 6, 9, 12, 14, 22 and 27). All samples remained negative after two blind passages in embryonated egg.

III. Serological results a. Hemagglutination Inhibition (H.I.) Antibody Titers

Fourteen days after the first administration, seroconversion was observed in six out of 10 subjects.

After the second administration, seven subjects out of 10 have seroconverted.

b. Serum Neutralization (S.N.) Antibody Titers

Fourteen days after the first administration, a significant antibody titer rise was noted in six out of 10 subjects, and after the second administration, in nine subjects out of 10.

When considering H.I. and S.N. titers, out of 10 volunteers, only one subject (No. 6) did not seroconvert after two administrations.

IV. Local antibodies

Local N antibody titers for all 10 subjects are given in Table III.

A significant antibody titer rise was observed in seven subjects out of nine, 14 days after the first administration and in eight out of 10, 21 to 28 days after the second inoculation.

TABLE II

Serum Antibodies and Clinical Manifestations.

| Subjects NO | Sex | H.I. antibodies before vaccin. | H.I. antibodies 14 days after 1st adm | H.I. antibodies 3–4 wks after 2nd adm | S.N. antibodies before vaccin. | S.N. antibodies 14 days after 1st adm | S.N. antibodies 3–4 wks after 2nd adm | Elevation of temperature | Clinical symptoms |
|---|---|---|---|---|---|---|---|---|---|
| 3 | F | 16 | 64 | 64 | 16 | 256 | 256 | 37.2° C on Day 1 | mild nasal congestion on day 1 and day 2. |
| 5 | M | <8 | <8 | 16 | 32 | 32 | 128 | None | — |
| 6 | F | 16 | 32 | 32 | 16 | 16 | 32 | None | slight headaches on day O (evening). Mild pharyngeal hypersecretion. |
| 9 | F | 8 | 8 | 16 | 16 | 16 | 64 | None | — |
| 12 | M | 8 | 16 | 16 | 8 | 16 | 32 | None | — |

TABLE II-continued

| Subjects NO | Sex | H.I. antibodies before vaccin. | H.I. antibodies 14 days after 1st adm | H.I. antibodies 3–4 wks after 2nd adm | S.N. antibodies before vaccin. | S.N. antibodies 14 days after 1st adm | S.N. antibodies 3–4 wks after 2nd adm | Elevation of temperature | Clinical symptoms |
|---|---|---|---|---|---|---|---|---|---|
| 14 | M | 8 | 32 | 64 | <8 | 64 | 64 | None | rhinitis - day 4 and 5 |
| 22 | M | 32 | 128 | 128 | 32 | ≥512 | ≥512 | None | rhinitis - day 1,2 and 3 |
| 23 | M | 16 | 128 | 128 | 16 | 256 | 256 | None | rhinitis - day 2 and 3 |
| 26 | M | 16 | 128 | 128 | 16 | 256 | 256 | None | rhinitis - day 0 evening |
| 27 | M | 8 | 32 | 32 | 16 | 64 | 64 | None | rhinitis - day 2 |

Serum Antibodies and Clinical Manifestations.

TABLE III

| Subjects NO | Local N Antibodies. Nasal washings (x) before vaccination | 14 days after 1st adm. | 3–4 weeks after 2nd adm. |
|---|---|---|---|
| 3 | <2 | 16 | 32 |
| 5 | <2 | 2 | 4 |
| 6 | <2 | 4 | 4 |
| 9 | <2 | 16 | ≤2 |
| 12 | <2 | <2 | 2 |
| 14 | <2 | 16 | 16 |
| 22 | <2 | 16 | ≥64 |
| 23 | <2 | NT | 8 |
| 26 | <2 | 64 | 128 |
| 27 | <2 | 8 | 4 |

(x) Nasal washings after standardization for immunoglobuline A (IgA) = about 200 μgr/ml.

I claim:

1. An attenuated influenza virus vaccine effective on intranasal administration comprising an effective amount of a serum inhibitor-resistant strain of influenza A virus obtained by passaging in the allantoic cavity of embryonated eggs a recombinant strain obtained from $H_3N_2$ influenza and A/$PR_8$ influenza, which strain is sensitive to serum inhibitors, said passaging being made in the presence of serum until a serum inhibitor resistant strain is obtained, and a carrier therefor.

2. A vaccine according to claim 1, where the $H_3N_2$ influenza strain is A/England/42/72.

3. A vaccine according to claim 2, where the A/$PR_8$ influenza strain is the Mount Sinai A/$PR_8$/34 strain.

4. A vaccine according to claim 3, where the recombinant is the MRC-2 strain.

5. A vaccine according to claim 4, wherein the embryonated eggs are embryonated chicken eggs.

6. A vaccine according to claim 5, where the serum is guinea pig serum.

7. A vaccine according to claim 6, where the passages are carried out in normal saline and by varying the serum and virus dilutions and isolating the virus from the culture having the highest serum concentration and highest virus dilution.

8. A method of preparing an attenuated influenza virus vaccine comprising incubating in the allantoic cavity of embryonated eggs a serum-inhibitor-resistant strain of influenza A Virus obtained according to claim 1, said incubation being for a period of time sufficient to permit growth of a larger amount of said virus strain and harvesting the resulting virus material.

* * * * *